United States Patent [19]

Molzahn et al.

[11] Patent Number: 5,387,708
[45] Date of Patent: Feb. 7, 1995

[54] PRODUCTION OF DIALKYL CARBONATES USING COPPER CATALYSTS

[75] Inventors: David C. Molzahn; Mark E. Jones; George E. Hartwell; Jose Puga, all of Midland, Mich.

[73] Assignee: The Dow Chemical Company, Midland, Mich.

[21] Appl. No.: 165,060

[22] Filed: Dec. 10, 1993

[51] Int. Cl.[6] .......................... C07C 69/96; B01J 31/18
[52] U.S. Cl. ..................................... 558/277; 502/164
[58] Field of Search ................ 558/277; 556/110, 113; 502/164

[56] References Cited

U.S. PATENT DOCUMENTS

| | | | |
|---|---|---|---|
| 4,625,044 | 11/1986 | Curnutt | 558/277 |
| 4,689,422 | 8/1987 | Sawicki et al. | 558/277 |
| 4,785,130 | 11/1988 | Bhattacharya | 558/277 |
| 4,900,705 | 2/1990 | Sawicki et al. | 502/158 |
| 5,001,252 | 3/1991 | Bhattacharya | 558/277 |
| 5,004,827 | 4/1991 | Curnutt | 558/277 |
| 5,132,259 | 7/1992 | Curnutt | 502/37 |
| 5,142,086 | 8/1992 | King, Jr. et al. | 558/274 |

FOREIGN PATENT DOCUMENTS

| | | |
|---|---|---|
| 0429675 | 6/1991 | European Pat. Off. . |
| 0534545 | 3/1993 | European Pat. Off. . |
| 64-13058 | 1/1989 | Japan . |
| 2256651 | 10/1990 | Japan . |

OTHER PUBLICATIONS

Mi-Yon Lee and Dae-Chul Park, "Alkylcarbonate Synthesis by New Catalytic System", in *Dioxygen Activation and Homogeneous Catalytic Oxidation, 1991*, L. I. Simandi, ed., 631.
Derwent 92-309696/38 (Sep. 16, 1992).
Derwent 83643C/47 (Oct. 11, 1980).
Derwent 86-001677/01 (Oct. 24, 1985) **translation of Examples 1,2, & 3 and Comparative Example 1.
Derwent 84-160152/26 (Jun. 27, 1984).
Derwent 35315C/20 (Mar. 31, 1980).
S. Sugiyama, et al., *Journal of Catalysis* 139, 338-350 (1993).

*Primary Examiner*—Mary C. Lee
*Assistant Examiner*—Michael G. Ambrose
*Attorney, Agent, or Firm*—Marie F. Zuckerman

[57] ABSTRACT

A process for the production of dialkyl carbonates, such as dimethyl carbonate. In one aspect, the process involves contacting under reaction conditions an alkanol, such as methanol, with carbon monoxide and oxygen in the vapor phase and in the presence of a catalyst containing (1) a copper halide, a copper oxyhalide, or a copper carboxylate halide, (2) a quaternary ammonium salt, and (3) a support component. The catalyst achieves high selectivity and productivity to dialkyl carbonates. In a second aspect, the addition of a chlorocarbon catalyst regenerator to the alkanol feed increases catalyst stability and lifetime and increases the selectivity and/or productivity to dialkyl carbonates.

30 Claims, No Drawings

PRODUCTION OF DIALKYL CARBONATES USING COPPER CATALYSTS

BACKGROUND OF THE INVENTION

This invention relates to the vapor phase production of dialkyl carbonates from alkanols, oxygen, and carbon monoxide.

Dialkyl carbonates, particularly dimethyl carbonate, are valuable commercial products finding utility as solvents and as precursors to polycarbonates and isocyanates. Dimethyl carbonate is also useful as a gasoline fuel additive.

U.S. Pat. No. 5,004,827 discloses a process of preparing dialkyl carbonates involving contacting carbon monoxide, oxygen and an alkanol in the vapor phase in the presence of a heterogeneous catalyst comprising cupric halide or a mixed cupric halide alkali metal halide supported on a suitable support, such as activated carbon. Disadvantageously, the productivity of the catalyst is low, and the catalyst lifetime is short. More disadvantageously, the carbon support is combustible. As a further disadvantage, the carbon support contributes to catalyst attrition. An attrition resistant catalyst is desirable for vapor phase processes, regardless of whether the process is conducted in a fixed, transport or fluidized bed reactor.

U.S. Pat. No. 4,625,044 discloses a process of preparing dialkyl carbonates involving contacting carbon monoxide, oxygen and an alcohol in the vapor phase and passing them over a catalytic amount of a copper coordination compound supported on activated carbon. The coordination compound comprises a nitrogen-containing organic compound copper hydrocarbyloxy halide, such as, pyridine copper methoxy chloride. Disadvantageously, the productivity of the catalyst is low. Moreover, the carbon support is combustible and contributes to catalyst attrition.

U.S. Pat. No. 4,785,130 teaches a process of preparing organic carbonates involving contacting an alcohol, such as methanol, and carbon monoxide in the presence of a catalyst containing copper hydrocarbonoxy halide, such as copper methoxy chloride, and a quaternary ammonium halide, such as benzyltriethylammonium chloride. Disadvantageously, this process is conducted in the liquid phase. Liquid phase reactions are oftentimes unattractive due to the corrosiveness of the reactants, products, or catalyst system. As a further disadvantage, this process is not truly catalytic. Moreover, recovery of the catalyst from the liquid phase is costly.

Japanese Patent Kokai No. H2-256,651 discloses the production of carbonic acid esters by reacting an alcohol with carbon monoxide and oxygen in the vapor phase in the presence of metallic copper, optionally supported on a support material. The catalyst is taught to be obtained by first adding a solid support material to a solution comprising a copper salt, such as a copper carboxylate, dissolved in water or an organic solvent. The resulting material is reduced and heat treated. Disadvantageously, the productivity of this catalyst is also low.

European Patent application 0,534,545 discloses a process for the production of dialkyl carbonates in which the catalyst is regenerated continuously. The process comprises contacting in the liquid phase an alcohol, carbon monoxide, and oxygen in the presence of cuprous chloride and hydrochloric acid. Disadvantageously, this process requires enameled reactors, because hydrochloric acid is corrosive.

It would be desirable to find an effective catalytic process for the production of dialkyl carbonates, such as dimethyl carbonate, wherein the productivity of the catalyst is high and the lifetime of the catalyst is long. It would be desirable if the process was conducted in the vapor phase, since that would eliminate problems associated with liquid phase processes. It would be more desirable if the process employed a heterogeneous catalyst which would eliminate the problems of catalyst recovery. It would be even more desirable if the catalyst used a support other than carbon, such as alumina or silica, because an inorganic support would reduce the problem of combustibility and minimize losses through attrition.

SUMMARY OF INVENTION

In one aspect this invention is a process for producing dialkyl carbonates which comprises contacting an alkanol, carbon monoxide, and oxygen in the vapor phase under reaction conditions such that a dialkyl carbonate is formed. The contacting is conducted in the presence of a catalytic amount of a catalyst comprising: (a) a copper halide, a copper oxyhalide, or a copper carboxylate halide, (b) a quaternary ammonium salt, and (c) a support component. The catalyst composition should satisfy three conditions. First, the atomic ratio of total halide to copper ($X^-/Cu$) should range from about 1.0 to about 3.0. Second, the atomic ratio of nitrogen to copper (N/Cu) should be greater than 0.0 but less than 2.0. Third, the catalyst should be essentially free of the platinum group metals. When the process of this invention is conducted as described hereinabove, the average productivity to dialkyl carbonates is greater than about 50 g/L-hr.

Advantageously, the process of this invention is conducted in the vapor phase, and therefore avoids the problems associated with liquid phase processes. More advantageously, the catalyst employed in the process of this invention is heterogeneous, which eliminates problems with catalyst recovery. Even more advantageously, the catalyst employed in the process of this invention may be prepared with non-carbon supports, such as alumina and silica, which lower catalyst attrition and combustibility. Most advantageously, the process of this invention achieves high selectivity and high productivity to dialkyl carbonates.

In a second aspect, this invention is an improved process of producing dialkyl carbonates which comprises contacting an alkanol, carbon monoxide, and oxygen in the vapor phase in the presence of a catalytic amount of a copper oxycarbonylation catalyst and in the presence of a promoting amount of an in situ catalyst regenerator, the contacting being conducted under reaction conditions such that the dialkyl carbonate is formed. The catalyst regenerator comprises a chlorocarbon compound containing chlorine which is labile under the process conditions.

Advantageously, the chlorocarbon regenerator continuously regenerates the copper catalyst in situ, thereby significantly increasing catalyst lifetime and stability in the oxycarbonylation process. Typically, a catalyst half-life greater than about 500 hr is achieved, and more preferably, greater than about 1000 hr. As a further advantage, the chlorocarbon compound acts as a promoter which significantly increases the selectivity and/or productivity to dialkyl carbonates. Even more advantageously, the positive effects of the chlorocarbon regenerator are essentially independent of the form of the catalyst, thus this improved mode of operation can be employed with any copper oxycarbonylation catalyst known for producing dialkyl carbonates from alkanols.

DETAILED DESCRIPTION OF THE INVENTION

In the process of this invention an alkanol, carbon monoxide, and oxygen are contacted in the vapor phase with a catalyst to produce dialkyl carbonates, as illustrated by the following equation for monoalkanols:

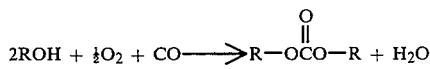

$$2ROH + \tfrac{1}{2}O_2 + CO \longrightarrow R-O\overset{\overset{O}{\|}}{C}O-R + H_2O$$

wherein ROH represents the alkanol, and R—OC-(O)O—R represents the dialkyl carbonate.

Alkanols useful in this invention include alkanols which are gaseous under reaction conditions. Preferred alcohols correspond to the formula ROH wherein R is $C_{1-6}$ alkyl or $C_{3-6}$ cycloalkyl. R is preferably $C_{1-6}$ alkyl. Examples of preferred alkanols include methanol, ethanol, propanol, butanol, pentanol, hexanol, cyclopropanol, cyclobutanol, cyclopentanol, and cyclohexanol. If a mixture of these alkanols is employed, then a mixture of symmetrical and asymmetrical dialkyl carbonates will be produced. A preferred asymmetrical dialkyl carbonate is methyl ethyl carbonate. Other preferred alkanols include diols of the formula HO—R$^1$—OH wherein R$^1$ is a $C_{2-4}$ alkyl moiety. Examples of suitable diols include ethylene glycol and propylene glycol. Diols such as these lead to hydroxy-terminated dialkyl or cyclic carbonate products. More preferably, the alkanol is methanol, ethanol, or propanol. Most preferably, the alkanol is methanol.

The catalysts employed in the process of this invention comprise certain supported copper compounds described hereinafter. Any support which will withstand the carbonylation conditions described herein may be employed. Preferably, therefore, the support is not a carbon support. Suitable supports include silica, alumina, silica-aluminas, magnesium silicate, barium silicate, gallium silicate, zirconium silicate, lanthanide silicates, such as lanthanum silicate and yttrium silicate, and aluminosilicate zeolites, such as zeolite Y. More preferred are alumina, yttrium silicate, and zeolite Y; most preferred are alumina and zeolite Y. Even more preferred is a support having a BET surface area greater than about 10 m$^2$/g, preferably, greater than about 50 m$^2$/g, and even more preferably greater than about 100 m$^2$/g. Preferably, the support has a surface area lower than about 1500 m$^2$/g, more preferably, lower than about 500 m$^2$/g, and most preferably lower than about 250 m$^2$/g. The BET surface area is the surface area as measured by the Brunauer-Mmmett-Teller method, which is described by R. B. Anderson in *Experimental Methods in Catalytic Research*, Academic Press, 1968, pp. 48-66.

Suitable copper compounds which can be employed in the process of this invention comprise the copper halides, wherein the copper is in the cuprous or cupric form. The halide can be chloride, bromide, iodide, or fluoride. More preferably, the halide is chloride or bromide, most preferably chloride. The preferred copper halide is cupric chloride. Other suitable copper catalysts for the process of this invention include copper oxyhalides, wherein the halide is as mentioned hereinbefore. The preferred copper oxyhalide is cupric oxychloride. For the purposes of this invention, the term "copper oxyhalide" includes protonated species, that is, cupric hydroxide halides.

Additional copper compounds which are suitable for the process of this invention comprise mixed copper carboxylate halide salts, provided that the salt has a solubility in water of greater than about 3 g Cu per 100 cc water. Such salts have sufficient solubility to achieve a copper loading on the support of greater than about 10 weight percent Cu by just one or two impregnations. The impregnation method for loading catalysts onto a support is disclosed in *Experimental Methods in Catalytic Research*, Vol II, edited by R. B. Anderson and P. T. Dawson, Academic Press, New York, 1978. Examples of mixed copper carboxylate halide salts having the required solubility include the copper formate halides and copper lactate halides. The halide can be chloride, bromide, iodide, or fluoride, and is most preferably chloride. The preferred copper carboxylate halide is cupric formate chloride.

The copper carboxylate halide can be prepared by reacting an aqueous suspension of cupric hydroxide chloride with formic or lactic acid. Alternatively, copper chloride can be reacted with sodium formate or sodium lactate. As a second alternative, basic copper salts, such as cuptic hydroxide or cupric carbonate, can be reacted with the carboxylic acid to yield copper carboxylate. The latter reacts with cupric chloride no yield copper carboxylate chloride.

Alternatively, mixed copper-transition metal carboxylate halide salts may be employed as the copper constituent of the catalyst. Suitable transition metals include the first row elements of Groups 7 through 12 of the Periodic Table, based on current IUPAC notation. These elements include manganese, iron, cobalt, nickel, copper, and zinc. Preferably, the transition metal is cobalt or zinc. The relative amount of transition metal ranges from about 0.1 to about 1.0 gram-atom percent based on the gram-atoms of copper present in the catalyst.

Any quaternary ammonium salt can be employed as the second constituent of the catalyst provided that the salt promotes the catalytic oxycarbonylation process of this invention. Preferred quaternary ammonium salts are represented by the formula $R^2{}_4N^+Y^-$ wherein each $R^2$ is independently a hydrocarbyl moiety selected from the group consisting of aliphatic, alicyclic, aryl and substituted aryl radicals and Y is halide, hydroxide or acetate. Preferably, each $R^2$ is independently a hydrocarbon moiety selected from the group consisting of $C_{1-6}$ alkyl, $C_{3-6}$ cycloalkyl, and $C_{6-15}$ aryl or substituted aryl moieties. More preferably, each $R^2$ is independently a $C_{1-3}$ alkyl. More preferably, Y is halide, including chloride, bromide, iodide, or fluoride. Most preferably, Y is chloride. Note that if Y is halide, it must be entered into the calculation of the atomic ratio $X^-/Cu$ defined hereinbefore. Suitable quaternary ammonium salts include tetramethylammonium chloride, tetraethylammonium chloride, phenyltrimethylammonium chloride, phenyltriethylammonium chloride, benzyltrimethylammonium chloride, benzyitriethylammonium chloride, and tetraethylammonium hydroxide, as well as the corresponding bromides, iodides, and fluorides. Most preferably, the quaternary ammonium salt is tetraethylammonium chloride or benzyltriethylammonium chloride.

As noted hereinabove, the atomic ratio of total halide to copper ($X^-$/Cu) in the catalyst employed in the process of this invention is required to range from about 1.0 to about 3.0, preferably, from about 1.5 to about 2.5. The atomic ratio of nitrogen to copper (N/Cu) is required to be greater than 0.0 but less than about 2.0, and preferably, is about 1.0.

It is possible for the quaternary ammonium salt and the copper halide, copper oxyhalide, or copper carboxylate halide to be combined in one cluster compound, provided that the cluster compound also satisfies the aforementioned atomic ratios $X^-$/Cu and N/Cu. The cluster compound can be synthesized before being applied to a suitable support. Suitable examples of cluster compounds include the tetrameric copper compounds $(R^3{}_4N)_4Cu_4(O)Cl_{10}$, wherein each $R^3$ is independently selected from $C_{1-6}$ alkyl, phenyl, and benzyl. Preferred tetrameric copper cluster compounds which satisfy this formula include $(Et_4N)_4Cu_4(O)Cl_{10}$ and $(Me_4N)_4Cu_4(O)Cl_{10}$, wherein Et and Me respectively stand for ethyl and methyl, as well as, the analogous benzyl triethyl and benzyl trimethyl ammonium copper clusters $[(PhCH_2)(Et_3)N]_4Cu_4(O)Cl_{10}$ and $[(PhCH_2)(Me_3)N]_4Cu_4(O)Cl10$. The phenyl trimethylammonium tetrameric copper cluster $[(Ph)(Me_3)N]_4Cu_4(O)Cl_{10}$ is also suitable. More preferably, the tetrameric copper cluster is $(Et_4N)_4Cu_4(O)Cl_{10}$ or $[(PhCH_2)(Et_3)N]_4Cu_4(O)Cl_{10}$. Also suitable as catalysts which satisfy the aforementioned required atomic ratios are simple stoichiometric salts, such as, tetraethylammonium copper chloride $(Et_4N)CuCl_3$, and tetramethylammonium copper chloride $(Me_4N)CuCl_3$.

The preparation of the tetrameric (tetramethylammonium)copper cluster compound is described by J. A. Bertrand and J. A. Kelley, in *Inorganic Chemistry*, 8 (9), (1969) 1982, incorporated herein by reference. This preparation can be generalized for the preparation of other tetrameric (tetraalkylammonium)copper cluster compounds. The stoichiometric monocopper salts are prepared from equimolar mixtures of copper halide and quaternary ammonium salt in a suitable solvent, such as methanol.

For the purposes of this invention, all of the aforementioned catalysts should be essentially free of the platinum group metals, namely, ruthenium, rhodium, palladium, osmium, iridium, and platinum. The term "essentially free" means that each platinum group metal comprises less than about 0.1 wt percent of the total catalyst composition including the weight of the support, and preferably, less than about 0.05 wt percent of the total catalyst composition.

Procedures known to those skilled in the art are employed to support the copper compounds and the quaternary ammonium salts. Typically, the copper compound and the quaternary ammonium salt are deposited on the carrier material by the impregnation method, as disclosed by R. B. Anderson and P. T. Dawson, in *Experimental Methods in Catalytic Research*, Vol II, op. cit.. For example, equimolar mixtures of cupric chloride or cupric carboxylate chloride and quaternary ammonium halide can be dissolved in a protic solvent, preferably methanol or water, and the resulting solution can be impregnated onto the desired support. Alternatively, the aforementioned copper cluster compounds can be synthesized and isolated, as described hereinabove, thereafter redissolved in a suitable solvent, and impregnated onto a support.

Another suitable method of preparing the catalyst of this invention involves heating the copper compound in the solid phase at a temperature sufficient to promote diffusion into the pores of a suitable support. Generally, the heating is conducted at a temperature between about 400° C. and about 700° C. Afterwards, the copper-loaded support is impregnated with a solution of the quaternary ammonium compound. In a variation of this method a solid mixture of the support and the copper compound are heated at a temperature between about 400° C. and about 700° C. for a time sufficient to load the desired amount of copper onto the support. The copper-loaded support is thereafter impregnated with a solution of the quaternary ammonium compound.

Generally, it has been found that a copper loading greater than about 0.03 g Cu/g catalyst results in active catalysts, that is, catalysts which achieve a productivity to dialkyl carbonates of greater than about 50 g/L-hr. The weight of the support component is included in the catalyst weight. Below this loading the activity of the catalyst may be too low for commercial purposes. Preferably, the copper loading is between about 0.05 and 0.15 g Cu/g catalyst, more preferably, between about 0.07 and 0.10 g Cu/g catalyst.

Any operable process conditions can be employed in this invention provided that dialkyl carbonates are produced. For example, the concentration of alkanol in the feedstream can be varied over a wide range. It is preferred, however, to keep the alkanol in the vapor phase and to avoid condensation. The preferred concentration of alkanol in the feedstream will therefore vary as a function of the process temperature and pressure. Typically, at a temperature between about 100° C. and about 140° C. and a pressure between about 250 psig and about 350 psig, the concentration of alkanol in the feedstream ranges from about 5 to about 30 mole percent, preferably from about 10 to about 20 mole percent.

The mole ratio of carbon monoxide to alkanol can be any mole ratio which results in the preparation of dialkyl carbonates. Preferably, the mole ratio of carbon monoxide to alkanol is between about 1:10 and about 100:1. More preferably, the mole ratio of carbon monoxide to alkanol is between about 1:2 and about 10:1, and most preferably, between about 1:1 and about 5:1.

Oxygen can be added to the reaction mixture as pure molecular oxygen or diluted with an inert gas such as nitrogen, helium, argon, or carbon dioxide. The concentration of oxygen in the feedstream typically ranges from about 2 to about 6 mole percent. Preferably, the concentration of oxygen in the feedstream is between about 2 and about 4 mole percent. Below about 2 mole percent, the conversion of methanol may be too low. Above about 6 mole percent, the oxygen concentration may fall within the flammability range.

The process of this invention can be performed at any operable temperature, pressure, and flow rate at which the reaction to dialkyl carbonates proceeds. Preferred temperatures are greater than about 90° C., but lower than about 200° C., with between about 100° C. and about 160° C. being more preferred. The most preferred temperature range falls between about 110° C. and 130° C. The pressure can be atmospheric or superatmospheric; however, the pressure should be low enough to maintain volatility. Preferred pressures are between about 1 and about 100 atmospheres, with between about 1 and about 50 atmospheres being most preferred. The reaction mixture feed gas flow rate, expressed as gas hourly space velocity (GHSV), can range between about 100 hr$^{-1}$ and about 20,000 hr$^{-1}$ and most preferably between about 500 hr$^{-1}$ and about 6,000 hr$^{-1}$.

The process of this invention can be performed in either a fixed or fluid bed reactor using either continuous or batch processing methods. It is preferred to use a fixed bed reactor and a continuous mode of operation.

When a monoalkanol is employed in the process of this invention, dialkyl carbonates are formed having the formula: R—OC(O)O—R wherein each R independently is as described hereinbefore in connection with the monoalkanol. Preferably, R is $C_{1-6}$ alkyl, more preferably, methyl, ethyl, or propyl, and most preferably, methyl. Examples of dialkyl carbonates prepared by the process of this invention include dimethyl carbonate, diethyl carbonate, dipropyl carbonate, dibutyl carbonate, dipentyl carbonate, dihexyl carbonate, dicyclopropyl carbonate, dicyclobutyl carbonate, dicyclopentyl carbonate, and dicyclohexyl carbonate. When mixtures of monoalkanols are employed in the process, a mixture of symmetrical and asymmetrical dialkyl carbonates is produced. Preferred asymmetrical carbonates include ethyl methyl carbonate and propyl methyl carbonate. When diols, such as $C_{2-4}$ diols, are employed in the process, cyclic carbonates, such as ethylene carbonate, are obtained. Preferred dialkyl carbonates prepared in accordance with this invention include dimethyl carbonate, diethyl carbonate, dipropyl carbonate, dibutyl carbonate, dipentyl carbonate, and dihexyl carbonate. More preferred products are dimethyl carbonate, diethyl carbonate, and dipropyl carbonate. The most preferred product is dimethyl carbonate.

The dialkyl carbonate can be recovered from the reaction mixture by methods well-known in the art, such as by azeotropic distillation, extractive distillation and simple distillation.

The process of this invention produces high gas phase conversions and yields based on converted methanol, as compared with prior art processes. A useful means for describing the efficacy of the process is by "productivity". As used herein, the "average DAC productivity" is defined as the grams of dialkyl carbonate produced per liter of catalyst per hour (g DAC/L-hr) averaged over the total run time. In the case of dimethyl carbonate, the units are given as g DMC/L-hr. In the practice of this invention, the average DAC productivity is greater than about 50 g DAC/L-hr. More preferably, the average productivity is greater than about 80 g DAC/L-hr. Even more preferably, the average productivity is greater than about 115 g DAC/L-hr. (To convert the average productivity from units of g DAC/L-hr into units of lb DAC/ft$^3$-hr, simply divide by a conversion factor of 16.016.) As used herein, the term "maximum productivity" is defined as the maximum number of grams of dialkyl carbonate produced per liter of catalyst per hour. The maximum productivity is typically greater than about 50 g DAC/L-hr, preferably, greater than about 150 g DAC/L-hr, and more preferably, greater than about 250 g DAC/L-hr.

Another useful indicator of the efficiency of the process of this invention is the selectivity to dialkyl carbonates. Here, selectivity can be calculated in one of two ways. The "DAC selectivity based on organics" is calculated by dividing the moles of dialkyl carbonate produced by the total moles of organic products produced containing carbon, oxygen, and hydrogen, and then multiplying by 100. In the oxidative carbonylation of methanol, the organic products produced will include dimethyl carbonate and may include as by-products dimethoxymethane, methyl formate, and dimethyl ether. Typically, the DAC selectivity, and especially the dimethyl carbonate (DMC) selectivity, based on organics is greater than about 85 mole percent. Preferably, the DAC selectivity based on organics is greater than about 90 mole percent, more preferably, greater than about 95 mole percent, and most preferably, greater than about 99 mole percent. The "DAC selectivity based on total products" is calculated by dividing the moles of dialkyl carbonate produced by the total moles of all products produced, excluding water, and then multiplying by 100. The total products produced, excluding water, are the above-identified organics as well as carbon dioxide. Typically, the DAC selectivity, and especially the dimethyl carbonate selectivity, based on total products is greater than about 40 mole percent, preferably, greater than about 50 mole percent, and more preferably, greater than about 70 mole percent.

The catalyst of this invention can be regenerated by treating the spent catalyst with gaseous hydrogen chloride, optionally in the presence of an inert gas, for a sufficient amount of time and at an appropriate temperature to effectively reactivate the catalyst. Typical inert gases useful for the regeneration include nitrogen, helium, carbon dioxide, and argon, with nitrogen or carbon dioxide being preferred. Typical regeneration temperatures range from about ambient temperature to about 300° C., and preferably from about ambient to about 150° C. The catalyst is subjected to hydrogen chloride from between about 0.1 to about 24 hours at a pressure between about 0.1 and about 500 psi. When an inert gas is used to dilute the halide, the hydrogen halide is present in the inert gas in a concentration ranging from about 0.1 to about 99 mole percent based on the inert gas, with between about 5 and about 20 mole percent of hydrogen halide being preferred. If desired, the regenerated catalyst may be freed of adsorbed HCl by purging with the inert gas. Optionally, prior to regeneration the spent catalyst may be dried in the presence of an inert gas so as to remove moisture. The drying is usually conducted at a temperature between about 90° C. and about 300° C. with about 115° C. to about 140° C. being preferred. More preferably, the regeneration with gaseous hydrogen chloride is conducted in the absence of methanol.

Surprisingly, it has now been found that the in situ regeneration of oxycarbonylation catalysts also takes place when a non-acid catalyst regenerator is fed continuously into the gaseous feedstream. The catalyst regenerator functions to replenish chlorine lost from the catalyst. In this way the catalyst lifetime and stability are significantly increased, and additionally, marked improvements in selectivity and/or productivity to dialkyl carbonates typically occur. Even more advantageously, the non-acid catalyst regenerator may be used to lengthen the lifetime of any oxycarbonylation catalyst which is capable of converting alkanols in the presence of carbon monoxide and oxygen to dialkyl carbonates, including those catalysts described herein and those described in the prior art. Prior art catalysts include, for example, cupric halides and mixed cupric alkali halides (in the absence of quaternary ammonium salts) described in U.S. Pat. No. 5,004,827, cupric alkoxy chlorides described in U.S. Pat. No. 4,785,130, and nitrogen-containing coordination compound copper hydrocarbyloxy halides described in U.S. Pat. No.

4,625,044, relevant sections of which are incorporated herein.

The catalyst regenerator comprises any chlorocarbon compound which contains a labile chlorine atom under the operating conditions of the process. The term "labile" means that the chlorine is capable of being transferred from the regenerator to the catalyst. Typically, the process operates at a temperature of less than about 140° C. At this temperature the carbon-chlorine covalent bond in the catalyst regenerator has a bond strength of less than about 80 Kcal. Suitable chlorocarbon compounds which function as catalyst regenerators include, but are not limited to, carbon tetrachloride, allyl chloride, pentachloroethane, and 1,1,1-trichloroethane. Preferably, the chlorocarbon catalyst regenerator is carbon tetrachloride. Typically, the catalyst regenerator comprises from 0.05 to about 5.0 weight percent of the feedstream, preferably, from about 0.1 to about 1.0 weight percent.

Catalysts treated with the chlorocarbon regenerator exhibit exceptionally long lifetimes. The extent to which the lifetime is improved will depend upon the specific catalyst used. Generally, a half-life of greater than about 500 hr is found. Preferably, the half-life is greater than about 1000 hr, and more preferably, greater than about 2500 hr. Additionally, in the presence of the chlorocarbon regenerator, the selectivity to dialkyl carbonates based on total products is typically increased by about 25 to about 400 percent. Another advantage is found in a significant increase in the average dialkyl carbonate productivity which can increase from about 10 percent to as much as about 800 percent.

The following examples are included for the purposes of illustration only and are not to be construed to limit the scope of the invention or claims. Unless otherwise indicated, all percentages are mole percent.

General Procedure for the Carbonylation of Methanol to Dimethyl Carbonate

The catalyst (5 cc) is loaded into a tubular reactor of Hastelloy C ($\frac{1}{4}'' \times 11''$). The catalyst is heated to a temperature between 100° C. and 150° C. under a flow of nitrogen. Appropriate flows of methanol vapor and carbon monoxide are established, and then air is introduced. The effluent gas is analyzed by gas chromatography using on-line sampling. Unless otherwise noted, the reaction temperature is 110° C., the pressure 300 psig, and the total gas flow is 350 sccm through 5 cc of catalyst. Unless otherwise noted, the gas composition is 36% carbon monoxide, 18% methanol, 2% oxygen and the balance nitrogen, by volume. The organic feed is either pure methanol or a dilute mixture of chlorinated hydrocarbon in methanol.

EXAMPLE 1

Cu(OCHO)Cl/Et$_4$NCl on Zeolite Y

A catalyst (5.00 grams) is prepared as follows: Cupric hydroxide chloride (CuOHCl, 12 g, 0.10 mole) is reacted with formic acid (6.0 g), and the mixture is diluted to 35 mL with water, then stirred until all material is dissolved. The resulting solution is added to zeolite Y bound with alumina in pelleted form (LZ-Y-84, 40.0 g). A small amount of unadsorbed solution is removed, and the pellets are allowed to air dry. The unadsorbed solution is diluted to 30 mL with water, and the pellets are impregnated with the solution to incipient wetness. The pellets are air dried prior to oven drying at 120° C. for 1 hour. Tetraethylammonium chloride hydrate (2.0 g, 0.01 mole) is dissolved in 4.5 g of water. The Cu-impregnated zeolite Y pellets are further impregnated to incipient wetness with the tetraethylammonium chloride solution. The impregnated pellets are air dried for 2 hours and dried for 1 hour at 120° C. to yield an oxycarbonylation catalyst having a Cl/Cu atomic ratio of 2 and a N/Cu atomic ratio of 1. Copper loading is 14 weight percent. The dried catalyst is ground to 14×30 mesh prior to loading into the reactor.

The catalyst (3.96 g) is loaded into the reactor described hereinabove. The oxycarbonylation of methanol is conducted under the process conditions and with the results shown in Table 1 (E-1a). Productivity averages 55.67 g/L-hr; DMC selectivity based on total products averages 49.53%. When 0.5 wt % carbon tetrachloride is added to the methanol feed, the average productivity increases to 76.54 g/L-hr, and the total selectivity increases to 71.67% (Table 1, E-1b).

TABLE 1[1,2]

| Run No. | Wt % Cl Cocat.[3] | Mole % DMC Selectivity, based on Organics | Mole % DMC Selectivity, based on Total Products | Avg DMC Productivity (g/L-hr) | Max DMC Prod. (g/L-hr) |
| --- | --- | --- | --- | --- | --- |
| E-1a | 0 | >99 | 49.53 | 55.67 | 66.65 |
| E-1b | 0.5 | >99 | 71.67 | 76.54 | 79.50 |
| E-2a | 0 | 97.01 | 53.44 | 88.87 | 135.73 |
| E-2b | 0.5 | >99 | 68.75 | 94.43 | 98.12 |
| CE-1 | 0 | 97.10 | 52.88 | 22.18 | 31.33 |
| E-3a | 0 | 87.23 | 50.57 | 52.76 | 54.71 |
| E-3b | 0.5 | 87.68 | 57.38 | 49.61 | 62.30 |
| E-4a | 0 | 99.45 | 69.66 | 86.96 | 122.76 |
| E-4b | 0.5 | >99 | 73.96 | 123.15 | 126.23 |
| CE-2 | 0 | >99 | 99.16 | 7.85 | 18.4 |
| E-5a | 0 | 95.80 | 54.40 | 119.42 | 378.31 |
| E-5b | 0 | 92.72 | 55.32 | 108.35 | 227.37 |
| E-5c | 0 | 90.09 | 61.24 | 130.17 | 234.26 |
| E-5d | 0.5 | 95.70 | 70.60 | 112.88 | 115.38 |
| E-6 | 0.5 | >99 | 68.16 | 179.94 | 309.84 |
| E-7a | 0 | 95.50 | 47.85 | 91.62 | 149.83 |
| E-7b | 0.5 | 99.90 | 73.75 | 207.50 | 237.02 |
| E-8a | 0 | 97.02 | 54.07 | 116.42 | 181.97 |
| E-8b | 0.5 | >99 | 70.07 | 161.69 | 170.45 |
| E-8c | 0.5 | >99 | 67.35 | 177.58 | 203.43 |
| E-8d | 1 | >99 | 71.29 | 136.33 | 152.72 |
| E-8e | 0.63 | >99 | 67.38 | 125.56 | 135.16 |
| E-9 | 0.5 | >99 | 70.98 | 145.52 | 174.20 |
| E-10a | 0 | 90.87 | 61.47 | 46.40 | 47.71 |
| E-10b | 0.5 | 94.16 | 73.68 | 45.16 | 46.34 |
| E-11 | 0.5 | >95 | 65 | 240 | 240 |

[1] Pressure, 300 psig with the exception of E-11 where pressure is 130 psig. Temperature, 110° C., with the exception of E-10a and E-10b where T = 135° C. and E-11 where T = 116° C.
[2] Gas flow E-1 to E-10, CE-1 and CE-2: Total flow, 350 sccm; MeOH flow, 63 sccm; Air flow, 35 sccm; CO flow, 127 sccm, with the exception of Examples 5c and 5d where CO flow is 32 sccm. Gas flow E-11: Total flow, 550 sccm; MeOH flow, 60 sccm; CO flow, 330 sccm; oxygen (10%) in nitrogen flow, 60 sccm; pure nitrogen flow, 100 sccm.
[3] Cl Cocatalyst: CCl$_4$ (1b, 2b, 3b, 4b, 5d, 6, 7b, 8b 8c, 9, 11), allyl chloride (8d), pentachloroethane (8e), 1,1,1-trichloroethane (10b).

EXAMPLE 2

CuCl/Et$_4$NCl on Zeolite Y

A catalyst is prepared as follows: Cuprous chloride (40 g) is mixed in a quartz container with zeolite Y bound with alumina as 1/16" extrudates (LZ-Y-85, 100 g). The quartz container is placed in a furnace and attached to a rotary drive unit to provide mixing during heating. The container is purged with nitrogen and heated rapidly to 300° C. under a continuous nitrogen purge. The temperature is then ramped from 300° C. to 625° C. over 90 minutes. The ramp rate is slowed and the temperature is increased from 625° C. to 650° over 15 minutes, where the temperature is held for 3 hours. The catalyst is then allowed to cool under nitrogen purge. Immediately prior to impregnation the copper zeolite is dried for 1 hour at 120° C. to reduce adsorbed moisture from the air. The copper zeolite (6.00 g) is then impregnated to incipient wetness with a solution of tetraethylammonium chloride hydrate (2.5 g) in 5.4 g of water. The catalyst is air dried for 16 hours and further dried at 120° C. for 2 hours. Cl/Cu ratio is 1.40 and N/Cu ratio is 0.61. Copper loading is 12.7 weight percent. The catalyst is ground to 14×30 mesh prior to loading into the reactor.

The catalyst (3.87g) is loaded into the reactor described hereinabove. The oxycarbonylation of methanol is conducted with the results shown in Table 1. Feeding pure methanol to the catalyst yields a DMC selectivity, based on total products, of 53.44% and an average productivity of 88.87 g/L-hr (E-2a). Addition of 0.5 weight percent carbon tetrachloride to the methanol feed (E-2b) increases the productivity to an average of 94.43 g/L-hr. Total selectivity is also increased.

COMPARATIVE EXPERIMENT 1

CuCl on Zeolite Y

A catalyst is prepared as in E-2, with the exception that the catalyst is not impregnated with tetraethylammonium chloride. The catalyst (3.39 g) is tested in the oxycarbonylation reactor with the results shown in Table I (CE-1). It is seen that the average DMC productivity is only 22.18 g/L-hr and the maximum DMC productivity is only 31.33 g/L-hr. When comparative experiment CE-1 is compared with Example E-2a, it is seen that the catalyst of E-2a prepared with the quaternary ammonium salt gives more than four times the productivity of DMC as the comparative catalyst prepared without the salt.

EXAMPLE 3

CuCl/Me$_4$NCl on Zeolite Y

A catalyst (6.00 g) is prepared as in E-2, with the exception that the catalyst is impregnated to incipient wetness with a solution of tetramethylammonium chloride (1.5 g) in 5.4 g of water in place of tetraethylammonium chloride. The catalyst has a Cl/Cu atomic ratio of 1.7 and N/Cu atomic ratio of 0.91. Copper loading is 12.8 weight percent.

The catalyst (3.91 g) is loaded into the reactor described hereinabove, and the oxycarbonylation of methanol is conducted with the results shown in Table 1. Feeding pure methanol (E-3a) or methanol containing 0.5 weight percent carbon tetrachloride (E-3b) to the catalyst produces roughly the same average DMC productivity, but the DMC selectivity based on total products increases in the presence of carbon tetrachloride.

EXAMPLE 4

CuCl$_2$/Et$_4$NCl on Alumina

Anhydrous cupric chloride (2.165 g, 16.10 mmoles) and tetraethylammonium chloride monohydrate (2.95 g, 16.10 mmoles) are added to 10.65 g methanol. Davison High SA alumina (10.0 g, 14×30 mesh) is impregnated to incipient wetness with the solution. The impregnated catalyst is air dried in methanol saturated air overnight. The catalyst exposed to ambient air to complete drying. The Cl/Cu atomic ratio is 3; N/Cu atomic ratio is 1. Copper loading based on amount of copper used is 6.90%.

The alumina supported catalyst (3.46 g) is loaded into the reactor described hereinabove, and the oxycarbonylation of methanol is conducted with the results shown in Table 1. Feeding pure methanol (E-4a) yields a DMC selectivity based on total products of 69.66 percent, and an average DMC productivity of 86.96 g/L-hr. The addition of 0.5 weight percent carbon tetrachloride to the methanol feed (E-4b) increases both the productivity and selectivity. The productivity remains constant when carbon tetrachloride is present.

COMPARATIVE EXPERIMENT

CuCl$_2$ on Alumina

A catalyst comprising copper chloride supported on alumina is prepared as in E-4 hereinabove, with the exception that the catalyst is not impregnated with tetraethylammonium chloride monohydrate. The catalyst (3.07 g) is tested in the oxycarbonylation of methanol with the results shown in Table I (CE-2). It is seen that the average DMC productivity is only 7.85 g/L-hr and the maximum DMC productivity is only 18.4 g/L-hr. When Comparative Experiment CE-2 is compared with Example E-4a, is it is seen that the average DMC productivity is eleven times greater and the maximum DMC productivity is more than 6 times greater when the catalyst is prepared with the quaternary ammonium salt.

EXAMPLE 5

(Et$_4$N)$_4$Cu$_4$OCl$_{10}$ on Alumina

Anhydrous cupric chloride (3.4 g) and cuptic oxide (2.0 g, powdered) are added to 75 mL of methanol in a 250 mL round bottomed flask. The resulting mixture is refluxed for 18 hours. Additional cupric chloride (6.8 g) is added and the solution is refluxed for 2 more hours. Tetraethylammonium chloride monohydrate (16.5 g) is added with stirring. The solution is concentrated under flowing nitrogen, and methylene chloride is added to redissolve the red solids which are collected. The copper complex which is formed, (Et$_4$N)$_4$Cu$_4$OCl$_{10}$, is then dissolved in 30 ml of a solution of approximately 3% methanol in methylene chloride. Alumina beads (10 g, Davison High SA, 196 m$^2$/g) are soaked in the solution for 20 hrs. The solvent is then evaporated to yield a catalyst having a Cl/Cu atomic ratio of 2.5 and N/Cu ratio of 1. Copper loading is 6 weight percent.

The alumina supported catalyst is crushed to 14×30 mesh and loaded (3.65 g) into the reactor described hereinabove. The oxycarbonylation of methanol is conducted with the results shown in Table 1. Feeding pure methanol (E-5a) initially produces dimethyl carbonate at very high levels (378.31 g/L-hr) which averages over time to 119.42 g/L-hr. After the catalyst is deactivated, it is removed from the reactor and exposed to the vapors above concentrated hydrochloric acid for several minutes. The catalyst is returned to the reactor, and dimethyl carbonate production is resumed (E-5b) at about the same average level as E-5a. A new charge of the same catalyst is loaded into the reactor and dimethyl carbonate production is initiated with less partial pressure of carbon monoxide than in the previous runs. The maximum DMC productivity is initially very high, exceeding 230 g/L-hr (E-5c), but the productivity falls over approximately 24 hours to less than 40 g/L-hr. The addition of 0.5 weight percent carbon tetrachloride to the methanol feed (E-5d) increases both the DMC productivity and selectivity. The productivity remains constant when carbon tetrachloride is present.

EXAMPLE 6

Et4N)4Cu4OCl10 on Silica

Finely divided cupric oxide is prepared by calcining basic copper carbonate at 500° C. in air for 2-3 hr. Anhydrous cupric chloride (1.99 g, 14.77 mmoles) and the finely divided cuptic oxide (0.39 g) are added to 15 mL of methanol in a round bottomed flask. The resulting mixture is refluxed for 2 hours. Tetraethylammonium chloride (3.26 g, 19.7 mmoles) is added with stirring to the flask, and the solution is refluxed for an additional hour to form the cluster complex (Et4N)-4Cu4OCl10. The solution is filtered and poured onto a silica support (Shell S-980-B1.5, 10.0 g) in a container. Sufficient methylene chloride is added to cover the support, about 50 mL, and the beads are sealed in the container for 16 hours. The remaining almost colorless solution is removed, and the catalyst is air dried. The catalyst thus prepared has a Cl/Cu atomic ratio of 2.5 and N/Cu ratio of 1.0. The dried catalyst weight indicates a loading of 7.39 weight percent Cu.

The silica supported catalyst is loaded (1.90 g) into the reactor described hereinabove. The oxycarbonylation of methanol is conducted with the results shown in Table 1 (E-6). The methanol feed contains 0.5 weight percent carbon tetrachloride. Average DMC productivity is 179.94 g/L-hr.

EXAMPLE 7

(BzEt3N)4Cu4OCl10 on Alumina

Finely divided cuptic oxide is produced as in Example 6. Anhydrous cupric chloride (8.07 g, 60 mmoles) and cuptic oxide (1.67 g, 21 mmoles) are added to 50 g of methanol in a round bottomed flask. The resulting mixture is refluxed for 23 hours. The solution is cooled and filtered. Benzyltriethylammonium chloride (5.47 g, 24 mmoles) is added to one third of the filtered solution forming a dark red solution. Slow addition of diethyl ether with stirring results in settling of a dark red, oily layer beneath a yellow/orange solution. The oily material is very soluble in methanol and yields a gummy solid upon evaporation of the methanol. A saturated methanol solution of the red solid, (BzEt3N)4Cu4OCl10, is made. This solution is used to impregnate alumina (Davison High SA, 5 grams, 14×30 mesh) to the point of incipient wetness. The catalyst is allowed to stand in methanol saturated air for 16 hours and is then air dried. Cl/Cu atomic ratio is 2.5 and N/Cu ratio is 1.0. Copper loading is 6.59 weight percent.

The alumina supported catalyst is loaded (3.20 g) into the oxycarbonylation reactor and tested in the oxycarbonylation of methanol with the results shown in Table 1. Feeding pure methanol (E-7a) initially produces dimethyl carbonate in excess of 149 g/L-hr with an average productivity of 91.62 g/L-hr over 24 hr. The addition of 0.5 weight percent carbon tetrachloride to the methanol feed (E-7b) significantly increases both the productivity and selectivity, as seen in Table I.

EXAMPLE 8

(Et4N)4Cu4OCl10 on Alumina

Finely divided cupric oxide is produced as in E-6. Anhydrous cuptic chloride (8.07 g, 60 mmoles) and cupric oxide (1.67 g, 21 mmoles) are added to 30 mL of methanol in a round bottomed flask. The resulting mixture is refluxed for 15 hours. The solution is cooled and tetraethylammonium chloride (14.70 g, 80 mmoles) is added and the solution refluxed for one hour. The solution is filtered to remove all solids. Slow addition of diethyl ether to the filtrate causes the precipitation of an oily red material. Addition of approximately 200 mL of ether causes the precipitate to become granular. The precipitate is collected by filtration. The collected solid, (Et4N)4Cu4OCl10 (2.77 g, 9.66 mmoles), is dissolved in methanol (6.39 g). The solution is used to impregnate alumina (Davison High SA, 6 g, 14×30 mesh) to the point of incipient wetness. The catalyst is exposed to methanol saturated air for 16 hours, and thereafter air dried. Cl/Cu atomic ratio is 2.5 and N/Cu ratio is 1.0. Copper loading is 6.74 weight percent.

The alumina supported catalyst is loaded (3.12 g) into the oxycarbonylation reactor and tested in the oxycarbonylation of methanol with the results shown in Table 1. Feeding pure methanol (E-8a) initially produces dimethyl carbonate in excess of 180 g/L-hr with an average productivity of 116 g/l-hr over 24 hr. The addition of 0.5 weight percent carbon tetrachloride to the methanol feed (E-Sb) significantly increases both the productivity and selectivity, as seen in the table. When operated with an initial liquid feed of 0.5 weight percent carbon tetrachloride in methanol, the productivity is initially high and stable (E-Sc). Changing the liquid feed to 1 weight percent allyl chloride in methanol also maintains selectivity and productivity (E-Sd). Changing the liquid feed to 0.63 weight percent pentachloroethane in methanol also maintains the selectivity and productivity (E-Be).

EXAMPLE 9

(Et4N)4Cu4OCl10 on Alumina

The tetrameric copper cluster (Et4N)4Cu4OCl10 (2.77 g, 9.66 mmoles), prepared as in E-8, is dissolved in methanol (6.39 g). The resulting solution is used to impregnate alumina (Davison High SA alumina, 6 g, 14×30 mesh) to the point of incipient wetness. The catalyst is left under methanol saturated air for 48 hr, and then dried at 120° C. for 30 min to yield the alumina supported tetrameric cluster containing 6.41 weight percent copper. The catalyst (3.03 g) is loaded into the oxycarbonylation reactor and tested in the oxycarbonylation of methanol with the results shown in Table I. For the entire duration of the run, 0.5 percent carbon tetrachloride in methanol is fed to the reactor. The catalyst shows only slight deactivation after 1000 hr of operation. Deactivation is measured at 0.0315 g/L-hr$^2$ yielding a half-life of greater than 2500 hr.

EXAMPLE 10

Cu(OCHO)Cl on Zeolite Y

Cu(OH)Cl (12 grams) is reacted with formic acid (6.0 g) and is diluted to 35 mL with water. The mixture is stirred until all material is dissolved. The resulting solution is added to alumina-bound pellets (40.0 g, LZ-Y-84). A small amount of unadsorbed solution is removed and the pellets are air dried. The unadsorbed solution is diluted with 30 mL of water, and the pellets are impregnated to incipient wetness. The pellets are air dried prior to oven drying at 120° C. for 1 hr. The finished catalyst is ground to 14×30 mesh.

The copper catalyst (4.51 g)) is tested in the oxycarbonylation of methanol with the results shown in Table I (E-10a). When 1,1,1-trichloroethane is added to the feedstream, the selectivity based on total products increases significantly (E-10b). This example shows that the chlorocarbon regenerator improves the oxycarbonylation process even in the absence of the quaternary ammonium salt.

EXAMPLE 11

Et$_4$NCuCl$_3$ on Alumina

Alumina (Davison, surface area 190 m$^2$/g) is impregnated with an equimolar solution of tetraethylammonium chloride and cupric chloride in methanol to form an oxycarbonylation catalyst. The dried catalyst contains 7.7 weight percent copper. The catalyst (3.19 g) is loaded into the oxycarbonylation reactor, and a flow of gaseous methanol containing 0.5 weight percent carbon tetrachloride (60 sccm) is introduced into the reactor. Thereafter, a gaseous flow comprising carbon monoxide (330 sccm), nitrogen (100 sccm), and a 10 volume percent mixture of oxygen in nitrogen (60 sccm) is initiated. Reactor temperature and pressure are maintained at 116° C. and 130 psig. Results are set forth in Table I. The production of dimethyl carbonate increases steadily during the first 10 hr to reach a stable DMC productivity of 240 g/L-hr with high selectivity to DMC.

What is claimed is:

1. A process of preparing dialkyl carbonates comprising contacting an alkanol, carbon monoxide, and oxygen in the vapor phase and in the presence of a catalytic amount of a catalyst, the contacting being conducted under reaction conditions such that a dialkyl carbonate is formed in an average productivity greater than about 50 g/L-hr, the catalyst comprising: (1) a copper halide, a copper oxyhalide, or a copper carboxylate halide, (2) a quaternary ammonium salt, and (3) a support component, wherein the atomic ratio of total halide to copper (X$^-$/Cu) in the catalyst ranges from about 1.0 to about 3.0 and the atomic ratio of nitrogen to copper (N/Cu) is greater than 0.0 but less than 2.0, and further wherein the catalyst is essentially free of the platinum group metals.

2. The process of claim 1 wherein the alkanol is ROH wherein R is a C$_{1-6}$ alkyl or C$_{3-6}$ cycloalkyl moiety or wherein the alkanol is HO—R$^1$—OH wherein R$^1$ is a C$_{2-4}$ alkyl moiety.

3. The process of claim 2 wherein the alkanol is methanol.

4. The process of claim 1 wherein the catalyst is supported on a non-carbon support selected from the group consisting of silica, alumina, silica-aluminas, aluminosilicate zeolites, and silicates of the lanthanide metals.

5. The process of claim 1 wherein the copper compound and the quaternary ammonium salt are combined in a cluster compound or a stoichiometric salt.

6. The process of claim 5 wherein the cluster compound is selected from tetrameric cluster compounds of the formula (R$_4$N)$_4$Cu$_4$(O)Cl$_{10}$ and wherein the stoichiometric salts have the formula (R$_4$N)CuCl$_3$ wherein R is a C$_{1-6}$ alkyl moiety, phenyl or benzyl.

7. The process of claim 6 wherein the cluster compound is (Et$_4$N)$_4$Cu$_4$(O)Cl$_{10}$.

8. The process of claim 6 wherein the stoichiometric salt is (Et$_4$N)CuCl$_3$.

9. The process of claim 1 wherein the copper compound is a copper carboxylate halide.

10. The process of claim 9 wherein the copper compound is copper formate halide or copper lactate halide.

11. The process of claim 1 wherein the copper carboxylate halide is combined with a transition metal halide wherein the transition metal is selected from the first row elements of Groups 7 through 12 of the Periodic Table.

12. The process of claim 1 wherein the loading of the copper on the catalyst composition ranges between about 0.05 and about 0.15 g Cu per g catalyst.

13. The process of claim 1 wherein the temperature ranges from about 90° C. to about 200° C. and the pressure ranges from about 1 atm to about 100 atm.

14. The process of claim 1 wherein the alkanol, carbon monoxide, and oxygen, and optionally a diluent gas, have a combined gas hourly space velocity of from about 100 hr$^{-1}$ to about 20,000 hr$^{-1}$.

15. The process of claim 1 wherein the selectivity to dialkyl carbonate, based on total organics, is greater than about 90 mole percent.

16. The process of claim 1 wherein the selectivity to dialkyl carbonate, based on total products, is greater than about 40 mole percent.

17. The process of claim 1 wherein the average productivity to dialkyl carbonate is greater than about 150 g/L-hr.

18. A process of preparing dimethyl carbonate comprising contacting methanol, carbon monoxide, and oxygen in the vapor phase and in the presence of a catalytic amount of a catalyst comprising: (1) a copper halide, copper oxyhalide, or copper carboxylate halide wherein the carboxylate is selected from formate or lactate, (2) a quaternary ammonium salt selected from tetramethylammonium chloride, tetraethylammonium chloride, and benzyltriethylammonium chloride, and (3) a non-carbon support component, wherein in the catalyst the atomic ratio of total halide to copper (X$^-$/Cu) ranges from about 1.0 to about 3.0 and the atomic ratio of nitrogen to copper (N/Cu) is greater than 0.0 but less than 2.0, and wherein the catalyst is essentially free of the platinum group metals; the contacting being conducted at a temperature between about 90° C. and about 200° C., a pressure between about 1 and about 100 atm, and a gas hourly space velocity between about 100 hr$^{-1}$ and about 20,000 hr$^{-1}$, such that dimethyl carbonate is formed in a productivity greater than about 50 g/L-hr.

19. A process of preparing a dialkyl carbonate wherein an alkanol, carbon monoxide, and oxygen are contacted in the vapor phase in the presence of a catalytic amount of a copper oxycarbonylation catalyst and in the presence of a promoting amount of a chlorocarbon catalyst regenerator, the contacting being conducted under reaction conditions such that a dialkyl carbonate is formed and the half-life of the catalyst is greater than about 500 hr.

20. The process of claim 19 wherein the alkanol is ROH wherein R is a C$_{1-6}$ alkyl or C$_{3-6}$ cycloalkyl moiety or the alkanol is HO—R$^1$—OH wherein R$^1$ is a C$_{2-4}$ alkyl moiety.

21. The process of claim 20 wherein the alkanol is methanol.

22. The process of claim 19 wherein the copper oxycarbonylation catalyst is selected from the group consisting of copper halides, copper oxyhalides, copper carboxylate halides, copper alkoxy halides, tetrameric copper cluster compounds of the formula (R$_4$N)$_4$Cu$_4$(O)Cl$_{10}$ and stoichiometric copper salts of the formula (R$_4$N)CuCl$_3$ wherein R is a C$_{1-6}$ alkyl moiety, phenyl or benzyl.

23. The process of claim 22 wherein the copper catalyst is $(Et_4N)_4Cu_4(O)Cl_{10}$.

24. The process of claim 22 wherein the copper catalyst is $(Et_4N)CuCl_3$.

25. The process of claim 19 wherein the temperature ranges from about 90° C. to about 200° C., the pressure ranges from about 1 arm to about 100 arm, and wherein the alkanol, carbon monoxide, oxygen, the chlorocarbon catalyst regenerator, and optionally an inert diluent gas, have a combined gas hourly space velocity of from about 100 hr$^{-1}$ to about 20,000 hr$^{-1}$.

26. The process of claim 19 wherein the chlorocarbon catalyst regenerator comprises from about 0.05 to about 5.0 weight percent of the vapor feedstream.

27. The process of claim 19 wherein the chlorocarbon catalyst regenerator is selected from the group consisting of carbon tetrachloride, allyl chloride, pentachloroethane, and 1,1,1-trichloroethane.

28. The process of claim 19 wherein the catalyst has a half-life greater than about 1000 hr.

29. An improved process of preparing dimethyl carbonate wherein a feedstream comprising methanol, carbon monoxide, and oxygen are contacted in the vapor phase in the presence of a catalytic amount of a copper-containing oxycarbonylation catalyst, the improvement comprising adding to the vapor feedstream a chlorocarbon catalyst regenerator selected from the group consisting of carbon tetrachloride, allyl chloride, pentachloroethane, and 1,1,1-trichloroethane in a concentration ranging from about 0.05 to about 5.0 weight percent and contacting the reactants at a temperature between about 90° C. and about 200° C., a pressure between about 1 and 100 atm, and a gas hourly space velocity between about 100 hr$^{-1}$ to about 20,000 hr$^{-1}$.

30. A catalyst composition comprising a copper compound selected from copper halides, copper oxyhalides, and copper carboxylate halides, (b) a quaternary ammonium salt, and (c) a non-carbon support, wherein the atomic ratio of total halide to copper ranges from about 1.0 to about 3.0 and wherein the atomic ratio of nitrogen to copper is greater than 0.0 but less than 2.0, the catalyst being essentially free of the platinum group metals.

* * * * *

UNITED STATES PATENT AND TRADEMARK OFFICE
CERTIFICATE OF CORRECTION

PATENT NO. : 5,387,708
DATED : Feb. 7, 1995
INVENTOR(S) : David C. Molzahn; Mark E. Jones; George E. Hartwell; Jose Puga It is certified that error appears in the above-indentified patent and that said Letters Patent is hereby corrected as shown below:

Claim 25, Column 17, line 7, please change "arm" both occurrences to correctly read "atm";

Claim 30, Column 18, line 14, please change "a" to correctly read "(a)"

Signed and Sealed this

Second Day of July, 1996

*Attest:*

BRUCE LEHMAN

*Attesting Officer*     *Commissioner of Patents and Trademarks*